United States Patent
Yu et al.

(10) Patent No.: US 6,824,786 B2
(45) Date of Patent: Nov. 30, 2004

(54) COMPOSITIONS COMPRISING PHENYL-GLYCINE DERIVATIVES

(76) Inventors: Ruey J. Yu, 4 Lindenwold Ter., Ambler, PA (US) 19002; Eugene J. Van Scott, 3 Hidden La., Abington, PA (US) 19001

( * ) Notice: Subject to any disclaimer, the term of this patent is extended or adjusted under 35 U.S.C. 154(b) by 222 days.

(21) Appl. No.: 10/294,741

(22) Filed: Nov. 15, 2002

(65) Prior Publication Data

US 2003/0108496 A1 Jun. 12, 2003

Related U.S. Application Data

(60) Provisional application No. 60/333,116, filed on Nov. 27, 2001.

(51) Int. Cl.[7] .......................... A61K 7/00; A61K 31/19; A61K 31/195
(52) U.S. Cl. ................... 424/401; 514/553; 514/557; 514/567
(58) Field of Search ................... 424/400, 401; 514/553, 557, 567, 844

(56) References Cited

U.S. PATENT DOCUMENTS

| | | |
|---|---|---|
| 4,492,683 A | 1/1985 | Nagpal |
| 4,918,064 A | 4/1990 | Cordi et al. |
| 5,258,391 A | 11/1993 | Van Scott et al. |
| 5,385,938 A | 1/1995 | Yu et al. |
| 5,389,677 A | 2/1995 | Yu et al. |
| 5,422,370 A | 6/1995 | Yu et al. |
| 5,470,880 A | 11/1995 | Yu et al. |
| 5,547,988 A | 8/1996 | Yu et al. |
| 5,554,597 A | 9/1996 | Yu et al. |
| 5,561,158 A | 10/1996 | Yu et al. |
| 5,643,959 A | 7/1997 | Pamukcu et al. |
| 5,665,776 A | 9/1997 | Yu et al. |
| 6,159,485 A | 12/2000 | Yu et al. |
| 6,261,544 B1 | 7/2001 | Coury et al. |
| 6,335,023 B1 | 1/2002 | Yu et al. |

*Primary Examiner*—Shelley A. Dodson
(74) *Attorney, Agent, or Firm*—Hunton & Williams LLP

(57) ABSTRACT

The invention relates to compositions and methods useful for treating a variety of cosmetic conditions and dermatological disorders, where the composition includes a phenyl glycine derivative represented by the following formula:

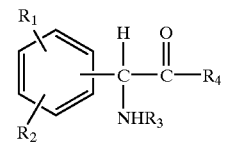

wherein, $R_1$ and $R_2$ are independently H, I, F, Cl, Br, OH, SH, $NH_2$, $NHNH_2$, alkyl, aralkyl, alkoxy, acetoxy, acyloxy group having 1 to 9 carbon atoms, and being attached at the 2, 3 or 4 position of the phenyl group, whereby when $R_1$ and/or $R_2$ are OH, SH, $NH_2$, they may be acetylated or acylated with 1 to 9 carbon atoms; $R_3$ is H, formyl, acetyl, propanoyl, acyl, alkyl, aralkyl or an aryl group having 1 to 9 carbon atoms; $R_4$ is OH, $NH_2$, NHOH, $NHNH_2$, or OR; where R is an alkyl, aralkyl or aryl group having 1 to 9 carbon atoms; the H attached to any carbon or nitrogen atom may be substituted by I, F, Cl, Br, OH, SH, $NH_2$, $NHNH_2$, an alkyl, aralkyl, alkoxy or acyl group having 1 to 9 carbon atoms. Phenyl-glycine and its derivatives may be present as isomeric D or L, non-isomeric or racemic DL, as a free acid, salt, lactone, amide or ester form.

87 Claims, No Drawings

COMPOSITIONS COMPRISING PHENYL-GLYCINE DERIVATIVES

This application claims the benefit of provisional application Ser. No. 60/333,116 filed Nov. 27, 2001.

FIELD OF THE INVENTION

The present invention relates to compositions comprising phenyl-glycine derivatives, methods of topically applying the compositions, as well as systemic use of the compositions for various skin conditions and diseases. The phenyl-glycine derivatives include 4-hydroxyphenyl-glycine, 4-hydroxyphenyl-glycinamide, 4-hydroxyphenyl-glycine esters, N-acetyl-4-hydroxyphenyl-glycine, N-acetyl-4-hydroxyphenyl-glycinamide, N-acetyl-4-hydroxyphenyl-glycine esters, N-acetyl-4-acetoxyphenyl-glycine, N-acetyl-4-acetoxyphenyl-glycinamide, N-acetyl-4-acetoxyphenyl-glycine esters and 4-acetoxyphenyl-glycinamide.

DESCRIPTION OF RELATED ART

Phenyl-glycine also is known as Phenyl-2-aminoethanoic acid. While all natural proteins are formed from about 20 common amino acids, the parent compound of the present invention, phenyl-glycine is not an amino acid found in such proteins. Phenyl-glycine compounds and compositions have been known to be useful, for example, as neurotoxic injury-reducing agents (U.S. Pat. No. 4,918,064), as photopolymerizable compound initiators (U.S. Pat. No. 6,261,544), as developing agents for photography, and for inhibiting the growth of fungi (U.S. Pat. No. 4,492,683). The disclosures of these patents are incorporated by reference herein in their entirety. These documents do not suggest the use of phenyl-glycine compounds and its derivatives for treating cosmetic disorders.

In our U.S. patent application Ser. No. 06/945,680, filed Dec. 23, 1986, entitled "Additives Enhancing Topical Actions of Therapeutic Agents," and related applications, issuing, inter alia, as U.S. Pat. Nos. 5,665,776, 5,389,677, and 5,422,370, we described and claimed compositions for and methods of enhancing the therapeutic effect of a cosmetic or pharmaceutical agent by using a hydroxyacid in combination with the agent. The disclosures of these documents are incorporated by reference herein in their entirety. The above-mentioned documents do not, however, disclose or suggest that a phenyl-glycine compound or derivative thereof would be useful for treating any skin conditions.

In our related U.S. patent application Ser. No. 07/683,437, filed Apr. 10, 1991, entitled "Compositions Comprising 2-Hydroxycarboxylic Acids and Related Compounds, and Methods for Alleviating the Signs of Dermatological Aging," and related applications, and issuing, inter alia, as U.S. Pat. Nos. 5,547,988, 5,554,597, and 5,561,158, we described and claimed the use of topical compositions containing a 2-hydroxycarboxylic acid or related compound for use in alleviating or improving the signs of aging, including the signs caused by intrinsic and extrinsic aging or extrinsic factors, of the skin, hair and nails. The disclosures of these documents are incorporated by reference herein in their entirety. These documents do not disclose or suggest, however, a phenyl-glycine compound or derivative thereof, or their use in treating any skin conditions.

In our U.S. Pat. No. 6,159,485 entitled "N-Acetyl Aldosamines, N-Acetylamino Acids and Related N-Acetyl Compounds and Their Topical Use," and our recent U.S. patent application No. 09/560,901, filed Apr. 28, 2000, entitled "N-Acetyl Aldosamines and Related N-Acetyl Compounds, and Their Topical Use," we described and claimed the use of N-acetyl derivatives of aminosugars and amino acids for topical treatment of various skin conditions and diseases. The amino acids were based on those commonly known 20 amino acids which are found in natural proteins. Although phenylalanine is a known amino acid present in natural proteins, phenyl-glycine is not known to exist in animal proteins and this compound has not been mentioned or implied for use in treating skin conditions.

It would be desirable to develop new and useful compounds and compositions that are useful in treating various skin conditions and disorders. It also would be desirable to develop new compounds and compositions useful in treating skin changes associated with aging, such as wrinkles, lack of elasticity, decreased collagen, and the like.

SUMMARY OF THE INVENTION

It therefore is a feature of an embodiment of this invention to provide methods and compositions comprising phenyl-glycine and its derivatives that are useful in topical as well as systemic treatment and prevention of various cosmetic conditions and dermatological disorders. Examples of cosmetic conditions and dermatological disorders may include, but are not limited to, promoting wound healing, general care of skin, hair, nail, oral, vaginal and anal mucosa, oral, gum diseases, dry skin, acne, ichthyosis, psoriasis, eczema and signs of aging, changes or damage to skin, nail and hair; the signs of skin, nail and hair changes associated with intrinsic and/or extrinsic aging.

The phenyl-glycine compounds and derivatives thereof of the present invention can be represented by the following generic formula:

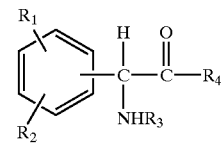

wherein, $R_1$ and $R_2$ are independently H, I, F, Cl, Br, OH, SH, $NH_2$, $NHNH_2$, alkyl, aralkyl, alkoxy, acetoxy, acyloxy group having 1 to 9 carbon atoms, and being attached at the 2, 3 or 4 position of the phenyl group, whereby when $R_1$ and/or $R_2$ are OH, SH, $NH_2$, they may be acetylated or acylated with 1 to 9 carbon atoms; $R_3$ is H, formyl, acetyl, propanoyl, acyl, alkyl, aralkyl or an aryl group having 1 to 9 carbon atoms; $R_4$ is OH, $NH_2$, NHOH, $NHNH_2$, or OR; where R is an alkyl, aralkyl or aryl group having 1 to 9 carbon atoms; the H attached to any carbon or nitrogen atom may be substituted by I, F, Cl, Br, OH, SH, $NH_2$, $NHNH_2$, an alkyl, aralkyl, alkoxy or acyl group having 1 to 9 carbon atoms. Phenyl-glycine and its derivatives may be present as isomeric D or L, non-isomeric or racemic DL, as a free acid, salt, lactone, amide or ester form.

Preferred phenyl-glycine derivatives useful in the compositions and methods of the invention preferably include 4-hydroxyphenyl-glycine, 4-hydroxyphenyl-glycinamide, 4-hydroxyphenyl-glycine methyl ester, 4-hydroxyphenyl-glycine ethyl ester, 4-hydroxyphenyl-glycine propyl ester, 4-hydroxyphenyl-glycine isopropyl ester, N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, N-acetyl-4-hydroxyphenyl-glycine propyl ester, N-acetyl-4-hydroxyphenyl-glycine isopropyl ester; N-acetyl-4-acetoxyphenyl-glycine, N-acetyl-4-acetoxyphenylglycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, N-acetyl-4-acetoxyphenyl-glycine isopropyl ester and 4-acetoxyphenyl-glycinamide.

In accordance with a feature of an embodiment of the invention, there is provided a cosmetic composition that includes a therapeutically effective amount of the above-mentioned phenyl-glycine compounds and derivatives. The composition of the present invention preferably includes the above-described phenyl-glycine compounds in combination with an excipient such as a pharmaceutically, cosmetically and/or topically acceptable carrier.

In accordance with another feature of an embodiment of the present invention, there is provided a method of improving, treating, ameliorating, alleviating, or reducing any of the above-mentioned and below-described cosmetic conditions and dermatological disorders comprising topically applying an effective amount of a composition comprising a phenyl-glycine compound or derivative thereof.

These and other features of the invention will be readily apparent to those skilled in the art upon reading the detailed description that follows.

DETAILED DESCRIPTION OF THE PREFERRED EMBODIMENTS

The present inventors have discovered that phenyl-glycine compounds and derivatives thereof are useful in treating a variety of cosmetic conditions and dermatological disorders. Phenyl-glycine also is known as phenyl-2-aminoacetic acid or phenyl-2-aminoethanoic acid which is not found in natural proteins. Natural proteins are formed from about 20 commonly known amino acids: glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan and proline. The amino acids such as glycine and phenylalanine are found as monopeptide units of natural polypeptides and proteins in the humans. However, phenyl-glycine is not found in any common natural polypeptides or proteins.

Compositions comprising the phenyl-glycine compounds and derivatives thereof are beneficial and effective for treating any of the cosmetic and dermatological disorders described in U.S. Pat. No. 6,335,023, the disclosure of which is incorporated by reference herein in its entirety. Specifically, the invention is useful for general care, reducing and soothing mucosa and skin erythema, inflammation or reaction caused by internal or external factors, treatment and healing of skin, hair, nail; nasal, oral and vaginal mucosa including treatment, healing and prevention of cosmetic conditions and dermatological indications as well as cosmetic and clinical signs of changes associated with intrinsic aging, or the damages caused by extrinsic factors as sunlight, radiations, air pollution, wind, cold, dampness, heat, chemicals, smoke, and cigarette smoking.

General care, reducing and soothing mucosa and skin erythema, inflammation or irritation caused by internal or external factors, treatment and healing of skin, hair, nail; nasal, oral and vaginal mucosa, and treatment, healing and prevention of cosmetic conditions and dermatological indications as well as cosmetic and clinical signs of changes associated with intrinsic aging, or the damages caused by extrinsic factors as sunlight, radiations, air pollution, wind, cold, dampness, heat, chemicals, smoke, and cigarette smoking may include blemished, irritated, inflamed, unhealthy, damaged or abnormal mucosa, skin, hair, nail, nostril, ear canal or vaginal conditions; oral or gum disease; disturbed keratinization; defective syntheses or repair of dermal components, and changes associated with intrinsic and extrinsic aging of skin, nail and hair. Those conditions and indications include dryness of the skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans and elastin as well as diminished levels of such components in the dermis; cellulite; stretch marks; skin lines; fine lines; wrinkles; thinning of skin, nail plate and hair; skin thickening due to elastosis of photoaging, loss or reduction of skin, nail and hair resiliency, elasticity and recoillability; lack of skin, nail and hair lubricants and luster; dull and older-looking skin, nail and hair; fragility and splitting of nail and hair.

The present inventors have discovered that phenyl-glycine and its derivatives have broad utilities for cosmetic conditions and dermatologic indications preferably including wound healing, general and specific conditions and indications involving skin, hair, nail, gum, oral, vaginal and anal mucosa. General cosmetic conditions and dermatological indications preferably include disturbed keratinization, inflammation, defective syntheses of dermal components, and changes associated with intrinsic and extrinsic aging of skin, nail and hair, and those indications that include, but are not limited to: dryness or looseness of skin, nail, and hair; xerosis; ichthyosis; palmar and plantar hyperkeratoses; uneven and rough surface of skin, nail, and hair; dandruff; Darier's disease; lichen simplex chronicus; keratoses; acne; pseudofolliculitis barbae; dermatoses; eczema; psoriasis; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans, and elastin, as well as diminished levels of these components in the dermis; stretch marks; skin lines; fine lines; wrinkles; thinning of skin, nail plate, and hair; skin thickening due to elastosis of photoaging; loss or reduction of skin, nail, and hair resiliency, elasticity and recoilability; lack of skin, nail, and hair lubricants and luster; dull and older-looking skin, nail, and hair; and fragility and splitting of nail and hair. The phenyl-glycine compounds or derivatives also can be used for skin lightening.

Specific skin changes associated with aging include progressive thinning of skin, fragile skin, deepening of skin lines and fine lines, wrinkles including fine and coarse wrinkles, lusterless skin surface, coarse and uneven skin, loss of skin elasticity and recoilability, blemished and leathery skin, loss of skin lubricating substances, increased numbers of blotches and mottles, nodules, pre-cancerous lesions, pigmented spots and mottled skin, changes in qualities and quantities of collagen and elastic fibers, solar elastosis, decrease in collagen fibers, diminution in the number and diameter of elastic fibers in the papillary dermis, atrophy of the dermis, stretch marks, reduction in subcutaneous adipose tissue and deposition of abnormal elastic materials in the upper dermis, yellowing skin, telangiectatic skin and older-looking skin. General care preferably includes prevention, maintenance and treatment of skin, oral, vaginal and anal mucosa, nail and hair, erythema, inflammation, itching, irritation caused by internal or external factors, including sunlight, radiations, ionizing radiations, air pollution, wind, cold, dampness, heat, chemicals, smoke, and cigarette smoking.

The phenyl-glycine and its derivatives also are useful for wound healing of skin, irritated or inflamed mucosa or skin; for skin lightening; for cleansing and conditioning of skin, hair and nail; for protection from extrinsic factors; for mouthwashes; for use as an antioxidant agent, toner, cleanser, moisturizer, emollient, protectant, foundation makeup, beauty masks, face powders, rouge, cover up, lipsticks, eye makeup, dentifrices, suntan preparation, soap preparation; as skin refinisher, to improve skin pores, flakiness and redness; to make skin soft, smooth, fresh, balanced, firm, visibly clear, even-toned and brighter.

In accordance with preferred embodiments of the invention, there is provided a composition comprising at least one compound selected from phenyl-glycine compounds and their derivatives, their free acids, esters, amides and salt forms, present in a therapeutically effective amount and in a topically acceptable vehicle for topical treatment of cosmetic conditions or dermatological disorders. In another embodiment of the invention, the composition further comprises a cosmetic, pharmaceutical or other topical agent, preferably providing an additive effect, and more preferably, a synergistic effect.

When the phenyl-glycine compounds of the present invention are used together with a cosmetic, pharmaceutical, or other topical agent, or combinations thereof, the composition preferably provides a synergistic effect, similar to that disclosed in U.S. Pat. No. 6,335,023, the disclosure of which is incorporated by reference herein in its entirety. Preferred cosmetic, pharmaceutical, or other topical agents include, for example, those that improve or eradicate age spots, keratoses and wrinkles, hydroxyacids, ketoacids and related compounds; phenyl alpha acyloxyalkanoic acids and derivatives; N-acetyl-aldosamines, N-acetylamino acids and related N-acetyl compounds; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratotic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; astringents; cleansing agents; corn, callus and wart removing agents; topical cardiovascular agents; vitamins; corticosteroids; tanning agents; humectants, hormones; retinoids; gum disease or oral care agents; dipilating agents; and other dermatologicals.

Preferred examples of the cosmetic, pharmaceutical and other topical agents include aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), aminocaproic acid, aminosalicylic acid, amitriptyline, anthralin, ascorbic acid, ascorbyl palmitate, atropine, azelaic acid, bacitracin, bemegride, beclomethasone dipropionate, benzophenone, benzoyl peroxide, betamethasone dipropionate, betamethasone valerate, brompheniramine, bupivacaine, butoconazole, calcipotriene, camphor, capsaicin, carbamide peroxide, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxycycline, doxepin, doxylamine, dyclonine, econazole, erythromycin, estradiol, ethinyl estradiol, fluocinonide, fluocinolone acetonide, 5-fluorouracil, griseofulvin, guaifenesin, haloprogin, hexylresorcinol, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichthammol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, oxybenzone, oxiconazole, oxymetazoline, padimate O, permethrin, pheniramine, phenol, phenylephrine, phenylpropanolamine, piperonyl butoxide, podophyllin, podofilox, povidone iodine, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, and zinc pyrithione. In addition, other topical agents that may be combined with phenyl-glycine or its derivatives include hydroxycarboxylic acids, O-acetyl-hydroxycarboxylic acids, oligosaccharide aldonic acids, N-acylamino sugars and N-acylamino acids, such as those disclosed in, for example, U.S. Pat. Nos. 5,258,391, 5,385,938, 5,422,370, 5,470,880, 5,547,988, 5,643,959, 6,159,485, and 6,335,023, the disclosures of each of which are incorporated by reference herein in their entirety. These agents may be used alone or in various combinations with one or more other agents.

Furthermore, in accordance with various features of the invention, there is provided a method for treating cosmetic conditions and dermatological disorders comprising topical as well as systemic administration of a composition comprising at least one compound selected from phenyl-glycine compounds and their derivatives, their free acids, esters, amides and salt forms in a topically acceptable vehicle. In one embodiment of the invention, the method comprises topically applying a therapeutically effective amount of a composition comprising at least one compound selected from phenyl-glycine compounds and their derivatives, their free acid, ester, amide and salts, and at least one cosmetic, pharmaceutical, or other topical agent in a topically acceptable vehicle.

In accordance with the present invention, the generic structure(s) or formula(s) of phenyl-glycine and its derivatives that are topically or systemically beneficial for various cosmetic and dermatological indications may be represented as follows:

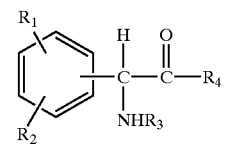

wherein, $R_1$ and $R_2$ are independently H, I, F, Cl, Br, OH, SH, $NH_2$, $NHNH_2$, alkyl, aralkyl, alkoxy, acetoxy, acyloxy group having 1 to 9 carbon atoms, and being attached at the 2, 3 or 4 position of the phenyl group, whereby when $R_1$ and/or $R_2$ are OH, SH, $NH_2$, they may be acetylated or acylated with 1 to 9 carbon atoms; $R_3$ is H, formyl, acetyl, propanoyl, acyl, alkyl, aralkyl or an aryl group having 1 to 9 carbon atoms; $R_4$ is OH, $NH_2$, NHOH, $NHNH_2$, or OR; where R is an alkyl, aralkyl or aryl group having 1 to 9 carbon atoms; the H attached to any carbon or nitrogen atom may be substituted by I, F, Cl, Br, OH, SH, $NH_2$, $NHNH_2$, an alkyl, aralkyl, alkoxy or acyl group having 1 to 9 carbon atoms. Phenyl-glycine and its derivatives may be present as isomeric D or L, non-isomeric or racemic DL, as a free acid, salt, lactone, amide or ester form.

The following are representative phenyl-glycine compounds that are useful in the present invention:
1. phenyl-glycine, phenyl-glycinamide, phenyl-glycine methyl ester, phenyl-glycine ethyl ester, phenyl-glycine propyl ester, and other esters;
2. N-acetyl-phenyl-glycine, N-acetyl -phenyl-glycinamide, N-acetyl-phenyl-glycine methyl ester, N-acetyl-phenyl-glycine ethyl ester, and other esters;
3. N-formyl-phenyl-glycine, N-formyl-phenyl-glycinamide, N-formyl-phenyl-glycine methyl ester, N-formyl-phenyl-glycine ethyl ester, and other esters;
4. N-propanoyl-phenyl-glycine, N-propanoyl-phenyl-glycinamide, N-propanoyl-phenyl-glycine methyl ester, N-propanoyl-phenyl-glycine ethyl ester, and other esters;
5. 4-hydroxyphenyl-glycine, 4-hydroxyphenyl-glycinamide, 4-hydroxyphenyl-glycine methyl ester, 4-hydroxyphenyl-glycine ethyl ester, and other esters;
6. N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, and other esters;
7. N-formyl-4-hydroxyphenyl-glycine, N-formyl-4-hydroxyphenyl-glycinamide, N-formyl-4-hydroxyphenyl-glycine methyl ester, N-formyl-4-hydroxyphenyl-glycine ethyl ester, and other esters;
8. N-propanoyl-4-hydroxyphenyl-glycine, N-propanoyl-4-hydroxyphenyl-glycinamide, N-propanoyl-4-hydroxyphenyl-glycine methyl ester, N-propanoyl-4-hydroxyphenyl-glycine ethyl ester, and other esters;
9. 4-acetoxyphenyl-glycine, 4-acetoxyphenyl-glycinamide, 4-acetoxyphenyl-glycine methyl ester, 4-acetoxyphenyl-glycine ethyl ester, and other esters;
10. N-acetyl-4-acetoxyphenyl-glycine, N-acetyl-4-acetoxyphenyl-glycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, and other esters;
11. N-formyl-4-acetoxyphenyl-glycine, N-formyl-4-acetoxyphenyl-glycinamide, N-formyl-4-acetoxyphenyl-glycine methyl ester, N-formyl-4-acetoxyphenyl-glycine ethyl ester, N-formyl-4-acetoxyphenyl-glycine propyl ester, and other esters;
12. N-propanoyl-4-acetoxyphenyl-glycine, N-propanoyl-4-acetoxyphenyl-glycinamide, N-propanoyl-4-acetoxyphenyl-glycine methyl ester, N-propanoyl-4-acetoxyphenyl-glycine ethyl ester, N-propanoyl-4-acetoxyphenyl-glycine propyl ester, and other esters;
13. 2-hydroxyphenyl-glycine, 2-hydroxyphenyl-glycinamide, 2-hydroxyphenyl-glycine methyl ester, 2-hydroxyphenyl-glycine ethyl ester, and other esters;
14. N-acetyl-2-hydroxyphenyl-glycine, N-acetyl-2-hydroxyphenyl-glycinamide, N-acetyl-2-hydroxyphenyl-glycine methyl ester, N-acetyl-2-hydroxyphenyl-glycine ethyl ester, and other esters;
15. N-formyl-2-hydroxyphenyl-glycine, N-formyl-2-hydroxyphenyl-glycinamide, N-formyl-2-hydroxyphenyl-glycine methyl ester, N-formyl-2-hydroxyphenyl-glycine ethyl ester, and other esters;
16. N-propanoyl-2-hydroxyphenyl-glycine, N-propanoyl-2-hydroxyphenyl-glycinamide, N-propanoyl-2-hydroxyphenyl-glycine methyl ester, N-propanoyl-2-hydroxyphenyl-glycine ethyl ester, and other esters;
17. N-acetyl-2-acetoxyphenyl-glycine, N-acetyl-2-acetoxyphenyl-glycinamide, N-acetyl-2-acetoxyphenyl-glycine methyl ester, N-acetyl-2-acetoxyphenyl-glycine ethyl ester, N-acetyl-2-acetoxyphenyl-glycine propyl ester, and other esters;
18. N-formyl-2-acetoxyphenyl-glycine, N-formyl-2-acetoxyphenyl-glycinamide, N-formyl-2-acetoxyphenyl-glycine methyl ester, N-formyl-2-acetoxyphenyl-glycine ethyl ester; N-formyl-2-acetoxyphenyl-glycine propyl ester, and other esters;
19. N-propanoyl-2-acetoxyphenyl-glycine, N-propanoyl-2-acetoxyphenyl-glycinamide, N-propanoyl-2-acetoxyphenyl-glycine methyl ester, N-propanoyl-2-acetoxyphenyl-glycine ethyl ester, N-propanoyl-2-acetoxyphenyl-glycine propyl ester, and other esters;
20. 3-hydroxyphenyl-glycine, 3-hydroxyphenyl-glycinamide, 3-hydroxyphenyl-glycine methyl ester, 3-hydroxyphenyl-glycine ethyl ester, and other esters;
21. N-acetyl-3-hydroxyphenyl-glycine, N-acetyl-3-hydroxyphenyl-glycinamide, N-acetyl-3-hydroxyphenyl-glycine methyl ester, N-acetyl-3-hydroxyphenyl-glycine ethyl ester, and other esters;
22. N-formyl-3-hydroxyphenyl-glycine, N-formyl-3-hydroxyphenyl-glycinamide, N-formyl-3-hydroxyphenyl-glycine methyl ester, N-formyl-3-hydroxy phenyl-glycine ethyl ester, and other esters;
23. N-propanoyl-3-hydroxyphenyl-glycine, N-propanoyl-3-hydroxyphenyl-glycinamide, N-propanoyl-3-hydroxyphenyl-glycine methyl ester, N-propanoyl-3-hydroxyphenyl-glycine ethyl ester, and other esters;
24. N-acetyl-3-acetoxyphenyl-glycine, N-acetyl-3-acetoxyphenyl-glycinamide, N-acetyl-3-acetoxyphenyl-glycine methyl ester, N-acetyl-3-acetoxyphenyl-glycine ethyl ester, N-acetyl-3-acetoxyphenyl-glycine propyl ester, and other esters;
25. N-formyl-3-acetoxyphenyl-glycine, N-formyl-3-acetoxyphenyl-glycinamide, N-formyl-3-acetoxyphenyl-glycine methyl ester, N-formyl-3-acetoxyphenyl-glycine ethyl ester, N-formyl-3-acetoxyphenyl-glycine propyl ester, and other esters;
26. N-propanoyl-3-acetoxyphenyl-glycine, N-propanoyl-3-acetoxyphenyl-glycinamide, N-propanoyl-3-acetoxyphenyl-glycine methyl ester, N-propanoyl-3-acetoxyphenyl-glycine ethyl ester, N-propanoyl-3-acetoxyphenyl-glycine propyl ester, and other esters;
27. 3,4-dihydroxyphenyl-glycine, 3,4-dihydroxyphenyl-glycinamide, 3,4-dihydroxyphenyl-glycine methyl ester, 3,4-dihydroxyphenyl-glycine ethyl ester, and other esters;
28. N-acetyl-3,4-dihydroxyphenyl-glycine, N-acetyl-3,4-dihydroxyphenyl-glycinamide, N-acetyl-3,4-dihydroxyphenyl-glycine methyl ester, N-acetyl-3,4-dihydroxyphenyl-glycine ethyl ester, and other esters; and
29. N-acetyl-3,4-diacetoxyphenyl-glycine, N-acetyl-3,4-diacetoxyphenyl-glycinamide, N-acetyl-3,4-diacetoxyphenyl-glycine methyl ester, N-acetyl-3,4-diacetoxyphenyl-glycine ethyl ester, and other esters.

The following are chemical structures of some representative phenyl-glycine derivatives

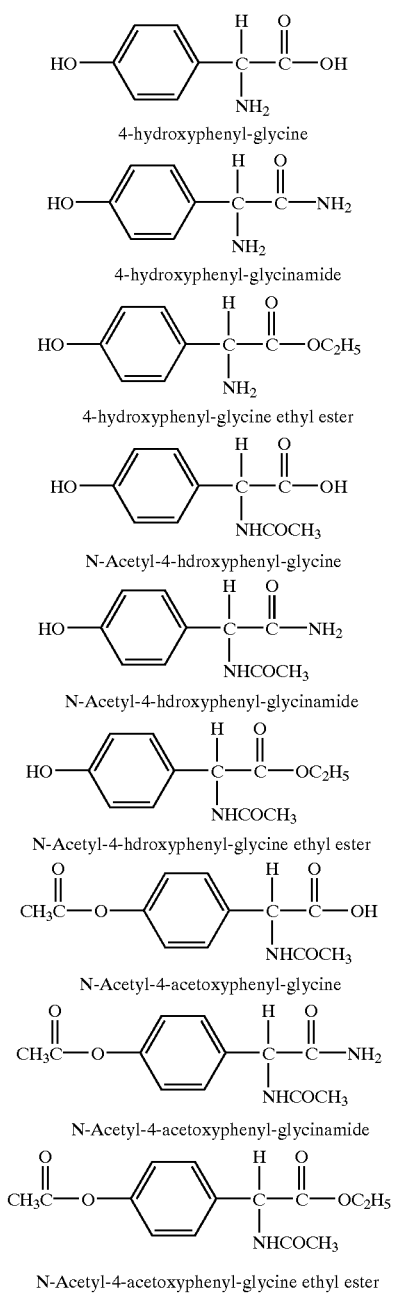

The above-described compounds, including those exemplified preferred compounds can be used alone or in combination with one another (or two others, or three others, or more) in the compositions of the present invention. The compositions of the invention can be prepared using conventional preparation techniques, depending on whether a lotion, cream, solution, spray, etc. is formed. Using the guidelines provided herein, those skilled in the art are capable of formulating any number of compositions using the phenyl-glycine compounds and derivatives described herein.

Compositions including a phenyl-glycine or its derivative of the instant invention may be formulated as solution, gel, lotion, cream, ointment, shampoo, spray, stick, powder, masque, mouth rinse or wash, vaginal gel or preparation, or other form acceptable for use on skin, nail, hair, oral mucosa, vaginal or anal mucosa, mouth or gums. To prepare a solution composition, at least one phenyl-glycine or its derivative of the instant invention preferably is dissolved in a solution prepared from water, ethanol, propylene glycol, butylene glycol, or other suitable solvents, and/or other topically acceptable vehicles.

The concentration of a single phenyl-glycine or its derivative or the total concentration of all phenyl-glycine derivatives where the composition comprises more than one phenyl-glycine derivative, preferably is a concentration sufficient to provide the desired cosmetic, topical or dermatological effect, which may vary depending on the desired topical or dermatological disorder being treated, the size of the patient, and other factors. Preferably, the concentration of phenyl-glycine derivative ranges from about 0.01 to about 99.9% by weight, based on the total weight of the composition, more preferably from about 0.1 to about 50% by weight, based on the total weight of the composition, and most preferably from about 0.5 to about 25% by weight, based on the total weight of the composition. Contemplated embodiments of the instant invention include ranges of 0.1% to 10%, 0.2% to 8%, 0.3% to 6%, 0.4% to 5%, 0.5% to 0.6%, 0.6% to 0.7%, 0.7% to 0.8%, 0.8% to 0.9%, 0.9% to 1%, 1% to 2%, 2% to 3%, 3% to 4%, 4% to 5%, 5% to 6%, 6% to 7%, 7% to 8%, 8% to 9%, 9% to 10%, 10% to 14%, 14% to 18%, 18% to 22%, 22% to 26%, 26% to 30%, 30% to 35%, 35% to 40%, 40% to 45%, 45% to 50%, 50% to 60%, 60% to 70%, 70% to 80%, 80% to 90%, and 90% to 99.9% by weight of the total composition. Those skilled in the art are capable of determining a suitable concentration of phenyl-glycine derivative, using the guidelines provided herein.

To prepare a topical composition in lotion, cream or ointment form, the phenyl-glycine or its derivative preferably is first dissolved in water, ethanol, propylene glycol, or other suitable solvent, and/or other vehicle, and the solution thus obtained is mixed with a desired base or pharmaceutically acceptable vehicle to make the lotion, cream or ointment. Concentrations of the phenyl-glycine or its derivative in lotion, cream, or ointment form are the same as those described above with respect to the concentration in solution.

A topical composition of the instant invention also may be formulated in a gel or shampoo form. A typical gel composition may be formulated by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate to a solution comprising the phenyl-glycine or its derivative. The preferred concentration of the gelling agent may range anywhere from about 0.1 to about 4% by weight, based on the total weight of the composition. In the preparation of the shampoo, the phenyl-glycine or its derivative preferably is first dissolved in water or propylene glycol, and the solution thus obtained is mixed with a shampoo base. Concentrations of the phenyl-glycine or its derivative used in gel or shampoo form are the same as those described above with respect to the concentration in solution.

To prepare a topical combination composition for additive or synergetic effects, a cosmetic, pharmaceutical or other topical agent is incorporated into any one of the above compositions by dissolving or mixing the agent into the formulation. Other forms of compositions for delivery of phenyl-glycine or its derivative of the instant invention may be readily blended, prepared or formulated by those skilled in the art. It is preferred in the invention that the combination of the claimed phenyl-glycine compound or its derivatives and a cosmetic, pharmaceutical or other topical agent provides a synergistic effect that is greater than the sum of the effects of any of the respective compounds when used alone.

For systemic use, the phenyl-glycine or its derivative can be formulated for oral administration or for parenteral injections. In oral preparations, the phenyl-glycine or its derivative can be formulated in tablet form or in gelatin capsules with or without mixing with gelatin powder. Each tablet or capsule can contain from 20 to 300 mg of a phenyl-glycine or its derivative. For parenteral injections the phenyl-glycine or its derivative preferably is prepared under sterilized conditions usually in 1 to 10% concentration in water and propylene glycol with a volume ratio of 7:3 or in fine suspension.

The following are illustrative examples of formulations and other aspects of the present invention. Although the examples utilize only selected compounds, formulations and test results, it should be understood that the following examples are illustrative and not limiting. Therefore, any of the aforementioned phenyl-glycine or its derivatives can be substituted according to the teachings of this invention in the following examples.

EXAMPLE 1

In one of the studies related to skin changes associated with aging, skin thickness was measured by micrometer calipers as follows:

The skin was grasped with a 2×6 cm metal hinge; the internal faces of which were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of two whole-skin layers. Triplicate measurements on treated sites were conducted and an average number was used for calculation of the skin thickness.

EXAMPLE 2

N-Acetyl-phenyl-glycine (5 g), was dissolved in ethanol (6 ml) and propylene glycol (6 ml), and the solution thus obtained was mixed uniformly with a cream base or oil-in-water emulsion (83 g). The cream thus formulated had a pH of 3.9 and contained 5% N-acetyl-phenyl-glycine.

EXAMPLE 3

4-Hydroxyphenyl-glycine (5 g) was dissolved in propylene glycol (15 ml), and the solution thus obtained was mixed uniformly with a cream base or oil-in-water emulsion (80 g). The cream thus formulated had a pH of 5.0 and contained 5% 4-hydroxyphenyl-glycine.

EXAMPLE 4

4-Hydroxyphenyl-glycine methyl ester (5 g) was dissolved in ethanol (15 ml) and propylene glycol (15 ml), and the solution thus obtained was mixed uniformly with a cream base or oil-in-water emulsion (65 g). The cream thus formulated had a pH of 4.3 and contained 5% 4-hydroxyphenyl-glycine methyl ester.

EXAMPLE 5

4-Hydroxyphenyl-glycine methyl ester (10 g) was dissolved in 90 ml solution prepared from ethanol (70 parts) and propylene glycol (30 parts by volume). The formulation thus prepared had a pH of 3.6 and contained 10% 4-hydroxyphenyl-glycine methyl ester.

EXAMPLE 6

4-Hydroxyphenyl-glycine methyl ester (7 g) was dissolved in 93 ml solution prepared from ethanol (70 parts) and propylene glycol (30 parts by volume). The formulation thus prepared had a pH of 4.1 and contained 7% 4-hydroxyphenyl-glycine methyl ester.

EXAMPLE 7

4-Hydroxyphenyl-glycine ethyl ester (5 g), gluconolactone (10 g), and arginine (2 g) were dissolved in 83 ml solution prepared from ethanol (40 parts), water (40 parts), and propylene glycol (20 parts by volume). The formulation thus prepared had a pH of 2.5 and contained 5% 4-hydroxyphenyl-glycine ethyl ester and 10% gluconolactone in an amphoteric composition.

EXAMPLE 8

4-Hydroxyphenyl-glycine ethyl ester (5 g) was dissolved in ethanol (10 ml) and propylene glycol (20 ml), and the solution thus obtained was mixed uniformly with a cream base or oil-in-water emulsion (65 g). The cream thus formulated had a pH of 4.3 and contained 5% 4-hydroxyphenyl-glycine ethyl ester.

EXAMPLE 9

N-Acetyl-4-hydroxyphenyl-glycine methyl ester (5 g) was dissolved in ethanol (16 ml) and propylene glycol (12 ml), and the solution thus obtained was mixed with a cream base or oil-in-water emulsion (67 g). The cream thus formulated had a pH of 2.8 and contained 5% N-acetyl-4-hydroxyphenyl-glycine methyl ester.

EXAMPLE 10

N-Acetyl-4-hydroxyphenyl-glycine ethyl ester (5 g) was dissolved in ethanol (10 ml) and propylene glycol (17 ml), and the solution thus obtained was mixed uniformly with a cream base or oil-in-water emulsion (68 g). The cream thus formulated had a pH of 2.5 and contained 5% N-acetyl-4-hydroxyphenyl-glycine ethyl ester.

EXAMPLE 11

N-acetyl-4-acetoxyphenyl-glycine (3 g) was dissolved in ethanol (12 ml), propylene glycol (5 ml) and water (5 ml), and the solution thus obtained was mixed uniformly with a cream base or oil-in-water emulsion (35 g). The cream thus formulated contained 5% N-acetyl-4-acetoxyphenyl-glycine.

EXAMPLE 12

N-Acetyl-4-hydroxyphenyl-glycinamide (10 g) was dissolved in warm ethanol (16 ml) and propylene glycol (12 ml), and the solution thus obtained was mixed uniformly with a cream base or oil-in-water emulsion (62 g). The cream thus formulated had a pH of 2.0 and contained 10% N-acetyl-4-hydroxyphenyl-glycinamide.

N-Acetyl-4-hydroxyphenyl-glycinamide (5 g) was dissolved in ethanol (10 ml) and propylene glycol (30 ml), and the solution thus obtained was mixed uniformly with a cream base or oil-in-water emulsion (55 g). The cream thus formulated had a pH of 2.4 and contained 5% N-acetyl-4-hydroxyphenyl-glycinamide.

EXAMPLE 13

N-Propanoyl-4-hydroxyphenyl-glycine (3 g) was dissolved in ethanol (12 ml) and propylene glycol (10 ml), and the solution thus obtained was mixed uniformly with a cream base or oil-in-water emulsion (35 g). The cream thus formulated had a pH of 3.8 and contained 5% N-propanoyl-4-hydroxyphenyl-glycine.

EXAMPLE 14

A male subject, age 30, having a severe dry skin condition of X-linked ichthyosis, with thick adherent scales since birth, had a 1 $cm^2$ area of involved skin of the back treated with N-acetyl-4-hydroxyphenyl-glycinamide 10% cream under Hays Occlusive Chamber. After one week, the Chamber was removed, and the treated site appeared normal, revealing an area of skin 2×2 cm which was now free of all evidence of ichthyosis. The treated site was left without any further treatment for another week, and at the end of which time the skin remained normal in clinical appearance.

The above result showed that N-acetyl-4-hydroxyphenyl-glycinamide was therapeutically effective for topical treatment of severe dry skin and as well as providing symptomatic relief of congenital ichthyosis.

EXAMPLE 15

A male subject, age 82, having chronic plaque psoriasis for 55 year duration resistant to all forms of topical therapy, topically applied N-acetyl-4-hydroxyphenyl-glycinamide 10% cream twice daily to a thick plaque of psoriasis on the right elbow. After five days of topical treatment, the erythema and thickness of the plaque had diminished substantially, and there was no evidence of any scales. The clinical evaluation was judged to be a 75% improvement after five days of topical treatment. After 13 days of topical treatment the skin of the treated area appeared to be clinically normal except for residual light pink color. Clinical evaluation rated the improvement to be about 90%.

The above result showed that N-acetyl-4-hydroxyphenyl-glycinamide was therapeutically effective for topical treatment of psoriasis.

EXAMPLE 16

N-Acetyl-4-hydroxyphenyl-glycinamide (3 g) and mandelic acid (2 g) were dissolved in 95 ml solution prepared from water (40 parts), ethanol (40 parts), and propylene glycol (20 parts by volume). The formulation thus prepared had a pH of 2.8 and contained 3% N-acetyl-4-hydroxyphenyl-glycinamide and 2% mandelic acid.

EXAMPLE 17

N-Acetyl-4-hydroxyphenyl-glycine methyl ester (5 g) and hydrocortisone -17-valerate (0.2 g) were dissolved in 95 ml solution prepared from ethanol (70 parts), and propylene glycol (30 parts by volume). The formulation thus prepared contained 5% N-acetyl-4-hydroxyphenyl-glycine methyl ester and 0.2% hydrocortisone-17-valerate.

EXAMPLE 18

N-Acetyl-4-hydroxyphenyl-glycine ethyl ester (5 g) and hydrocortisone -17-valerate (0.2 g) were dissolved in 95 ml solution prepared from ethanol (70 parts) and propylene glycol (30 parts by volume). The formulation thus prepared contained 5% N-acetyl-4-hydroxyphenyl-glycine ethyl ester and 0.2% hydrocortisone-17-valerate.

EXAMPLE 19

4-Hydroxyphenyl-glycine ethyl ester (5 g) and hydrocortisone-17-valerate (0.2 g) were dissolved in 95 ml solution prepared from ethanol (70 parts) and propylene glycol (30 parts by volume). The formulation thus prepared contained 5% 4-hydroxyphenyl-glycine ethyl ester and 0.2% hydrocortisone-17-valerate.

EXAMPLE 20

A male subject, age 70, with nummular eczema on his right lower leg for several years duration had intense itch on skin lesions that responded with partial relief to conventional anti-itch and anti-eczema agents. The subject topically applied N-acetyl-4-hydroxyphenyl-glycinamide 5% cream. A few minutes after the topical application, the severe itch disappeared completely and the lesions remained free of itch for the next 12 hours. On continued topical application of the cream twice daily for two weeks, the eczematous lesions improved substantially as determined by clinical evaluation. The above result showed that N-acetyl-4-hydroxyphenyl-glycinamide was therapeutically effective for topical treatment of eczema as well as eradication of pruritus.

EXAMPLE 21

A male subject, age 70, with chronic urticaria on his right hand for two months duration had intense itch on skin lesions which did not respond to conventional anti-itch agents. The subject topically applied N-acetyl-4-hydroxyphenyl-glycinamide 5% cream. A few minutes after the topical application, the severe itch disappeared completely and the lesions remained free of itch for the next 12 hours. The above result showed that N-acetyl-4-hydroxyphenyl-glycinamide was therapeutically effective for topical treatment of pruritus.

EXAMPLE 22

A male subject, age 70, with acute itchy rash on his right hand topically applied N-acetyl-4-hydroxyphenyl-glycine ethyl ester 5% cream. A few minutes after the topical application, the severe itch disappeared completely and the lesions remained free of itch and rash for the next 8 hours. The above results showed that N-acetyl-4-hydroxyphenyl-glycine ethyl ester was therapeutically effective for topical treatment of contact dermatitis.

EXAMPLE 23

A male subject, age 30, having a severe dry skin condition of X-linked ichthyosis, with thick adherent scales since birth, had a 1 $cm^2$ area of involved skin of the back treated with 4-hydroxyphenyl-glycine methyl ester 10% cream under Hays Occlusive Chamber. After one week, the Chamber was removed, and the treated site appeared normal, revealing an area of skin 2×2 cm which was now free of all evidence of ichthyosis. The treated site was left without any further treatment for another week, and at the end of which time the skin remained normal in clinical appearance. The same topical effect was also achieved with 10% cream containing 4-hydroxyphenyl-glycine ethyl ester under the same condition.

The above results showed that 4-hydroxyphenyl-glycine methyl ester and 4-hydroxyphenyl-glycine ethyl ester were therapeutically effective for topical treatment of severe dry skin and as well as providing symptomatic relief of congenital ichthyosis.

EXAMPLE 24

N-Acetyl-4-acetoxyphenyl-glycinamide (5 g) was dissolved in ethanol (10 ml), propylene glycol (30 ml), and water (5 ml) and the solution thus obtained was mixed uniformly with a cream base or oil-in-water emulsion (50 g). The cream thus formulated had a pH of 3.5 and contained 5% N-acetyl-4-acetoxyphenyl-glycinamide.

EXAMPLE 25

Three patients having chronic plaque psoriasis resistant to most forms of topical therapy topically applied N-acetyl-4-acetoxyphenyl-glycinamide 5% cream (Example 24) twice daily to thick plaques of psoriasis. After one week of topical treatment, the erythema and thickness of the plaques had diminished substantially, and there was no evidence of any psoriatic scales. The clinical evaluation was judged to be an 80% improvement after one week of topical treatment. After two weeks of topical treatment the skin of the treated area appeared to be clinically normal. Clinical evaluation rated the improvement on three patients to be from 95 to 100%.

The above results showed that N-acetyl-4-acetoxyphenyl-glycinamide was therapeutically effective for topical treatment of psoriasis.

EXAMPLE 26

For oral administration gelatin capsules containing phenyl-glycine or its derivatives in different doses can be prepared as follows.

N-Acetyl-4-acetoxyphenyl-glycinamide was milled into fine powder, and gelatin capsules size No. 1 were filled to the top with the powder. Each gelatin capsule thus filled contained approximately 200 mg of N-acetyl-4-acetoxyphenyl-glycinamide. Prepared under the same conditions, each gelatin capsule contained 270 mg and 250 mg of 4-hydroxyphenyl-glycine ethyl ester and N-acetyl-4-hydroxyphenyl-glycine methyl ester, respectively. Using a smaller capsule size, each gelatin capsule contained approximately 70 mg of N-acetyl-4-acetoxyphenyl-glycinamide. A suggested oral dosage for N-acetyl-4-hydroxyphenyl-glycinamide and N-acetyl-4-acetoxyphenyl-glycinamide is about 1-3 mg/kg body weight daily.

EXAMPLE 27

N-Acetyl-4-hydroxyphenyl-glycine (5 g) was dissolved in ethanol (20 ml) and propylene glycol (8 ml), and the solution thus obtained was mixed uniformly with a cream base or oil-in-water emulsion (67 g). The cream thus formulated had a pH of 3.2, and contained 5% N-acetyl-4-hydroxyphenyl-glycine.

EXAMPLE 28

N-Acetyl-4-acetoxyphenyl-glycine (5 g) was dissolved in ethanol (20 ml), propylene glycol (8 ml) and water (8 ml), and the solution thus obtained was mixed uniformly with a cream base or oil-in-water emulsion (59 g). The cream thus formulated had a pH of 1.5 and contained 5% N-acetyl-4-acetoxyphenyl-glycine.

EXAMPLE 29

4-Hydroxyphenyl-glycine ethyl ester (5 g), gluconolactone (10 g), and arginine (2 g) were dissolved in 83 ml solution prepared from ethanol (40 parts), water (40 parts), and propylene glycol (20 parts by volume). The formulation thus prepared had a pH of 2.5, and contained 5% 4-hydroxyphenyl-glycine ethyl ester and 10% gluconolactone in an amphoteric composition.

EXAMPLE 30

A female subject, age 75, applied topically twice daily N-acetyl-4-hydroxyphenyl-glycinamide 5% cream to her left forearm for eight weeks. After eight weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 49% in skin thickness as measured by the micrometer calipers (Example 1). This result indicated that N-acetyl-4-hydroxyphenyl-glycinamide would be therapeutically effective for topical treatment of wrinkles and changes of skin, nail or hair associated with aging.

EXAMPLE 31

A female subject, age 63, applied topically twice daily N-acetyl-4-hydroxyphenyl-glycinamide 10% cream to her left forearm for six weeks. After six weeks her untreated right forearm was still loose, relatively thin and wrinkled when lifted. In contrast, her left forearm was more firm, smooth, plump and minimally wrinkled when lifted. While there was no change in skin thickness of her right forearm, her left forearm had increased 24% in skin thickness as measured by the micrometer calipers (Example 1). This result indicated that N-acetyl-4-hydroxyphenyl-glycinamide would be therapeutically effective for topical treatment of wrinkles and changes of skin, nail or hair associated with aging.

EXAMPLE 32

A female subject, age 48, applied topically twice daily N-acetyl-4-acetoxyphenyl-glycinamide 10% cream to her right forearm for four weeks. After four weeks her untreated left forearm was still loose, relatively thin and wrinkled when lifted. In contrast, her right forearm was more firm, smooth, plump and minimally wrinkled when lifted. While there was no change in skin thickness of her left forearm, her right forearm had increased 25% in skin thickness as measured by the micrometer calipers (Example 1). This result indicated that N-acetyl-4-acetoxyphenyl-glycinamide would be therapeutically effective for topical treatment of wrinkles and changes of skin, nail or hair associated with aging.

While the invention has been described with reference to particularly preferred examples and embodiments, those skilled in the art will appreciate that various modifications may be made to the invention without departing from the spirit and scope thereof.

What is claimed is:

1. A composition comprising a therapeutically effective amount of a phenyl glycine derivative represented by the following formula:

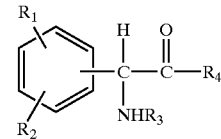

wherein, $R_1$ and $R_2$ are independently H, I, F, Cl, Br, OH, SH, $NH_2$, $NHNH_2$, alkyl, aralkyl, alkoxy, acetoxy, acyloxy group having 1 to 9 carbon atoms, and being attached at the 2, 3 or 4 position of the phenyl group, whereby when $R_1$ and/or $R_2$ are OH, SH, $NH_2$, they may be acetylated or acylated with 1 to 9 carbon atoms; $R_3$ is H, formyl, acetyl, propanoyl, acyl, alkyl, aralkyl or an aryl group having 1 to 9 carbon atoms; $R_4$ is OH, $NH_2$, NHOH, $NHNH_2$, or OR; where R is an alkyl, aralkyl or aryl group having 1 to 9 carbon atoms; the H attached to any carbon or nitrogen atom may be substituted by I, F, Cl, Br, OH, SH, $NH_2$, $NHNH_2$, an alkyl, aralkyl, alkoxy or acyl group having 1 to 9 carbon atoms. Phenyl-glycine and its derivatives may be present as isomeric D or L, non-isomeric or racemic DL, as a free acid, salt, lactone, amide or ester form, and an excipient.

2. The composition as claimed in claim 1, wherein the phenyl-glycine derivative is selected from the group consisting of 4-hydroxyphenyl-glycine, 4-hydroxyphenyl-glycinamide, 4-hydroxyphenyl-glycine methyl ester, 4-hydroxyphenyl-glycine ethyl ester, 4-hydroxyphenyl-glycine propyl ester, 4-hydroxyphenyl-glycine isopropyl ester, N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, N-acetyl-4-hydroxyphenyl-glycine propyl ester, N-acetyl-4-hydroxyphenyl-glycine isopropyl ester; N-acetyl-4-acetoxyphenyl-glycine, N-acetyl-4-acetoxyphenyl-glycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, N-acetyl-4-acetoxyphenyl-glycine isopropyl ester, 4-acetoxyphenyl-glycinamide, and mixtures thereof.

3. The composition as claimed in claim 1, wherein the phenyl-glycine derivative is N-Acetyl-4-hydroxyphenyl-glycinamide.

4. The composition as claimed in claim 1, wherein the phenyl-glycine derivative is N-acetyl-4-acetoxyphenyl-glycinamide.

5. The composition as claimed in claim 1, wherein the phenyl-glycine derivative is 4-hydroxyphenyl-glycine methyl ester.

6. The composition as claimed in claim 1, wherein the phenyl-glycine derivative is 4-hydroxyphenyl-glycine ethyl ester.

7. The composition as claimed in claim 1, wherein the phenyl-glycine derivative is N-acetyl-4-hydroxyphenyl-glycine ethyl ester.

8. The composition as claimed in claim 1, wherein the composition is selected from the group consisting of a solution, a gel, a lotion, a cream, an ointment, a shampoo, a spray, a stick, a powder, a masque, a mouth rinse or wash, a vaginal gel or preparation, in solution or suspension for injection, in tablet or capsule form for oral administration, and mixtures and combinations thereof.

9. The composition as claimed in claim 1, wherein the composition further comprises one or more additional ingredients selected from the group consisting of cosmetic agents, pharmaceutical agents, topical agents, and mixtures and combinations thereof.

10. The composition as claimed in claim 9, wherein the one or more additional ingredients is selected from the group consisting of agents that improve or eradicate age spots, keratoses, and/or wrinkles; hydroxyacids, ketoacids and related compounds; phenyl alpha acyloxyalkanoic acids and derivatives; N-acetyl-aldosamines, N-acetylamino acids and related N-acetyl compounds; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratotic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; astringents; cleansing agents; corn, callus and wart removing agents; topical cardiovascular agents; vitamins; corticosteroids; tanning agents; humectants, hormones; retinoids; gum disease or oral care agents; dipilating agents; and other dermatologicals.

11. The composition as claimed in claim 9, wherein the one or more additional ingredients is selected from the group consisting of aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), aminocaproic acid, aminosalicylic acid, amitriptyline, anthralin, ascorbic acid, ascorbyl palmitate, atropine, azelaic acid, bacitracin, bemegride, beclomethasone dipropionate, benzophenone, benzoyl peroxide, betamethasone dipropionate, betamethasone valerate, brompheniramine, bupivacaine, butoconazole, calcipotriene, camphor, capsaicin, carbamide peroxide, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxycycline, doxepin, doxylamine, dyclonine, econazole, erythromycin, estradiol, ethinyl estradiol, fluocinonide, fluocinolone acetonide, 5-fluorouracil, griseofulvin, guaifenesin, haloprogin, hexylresorcinol, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichthammol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, oxybenzone, oxiconazole, oxymetazoline, padimate O, permethrin, pheniramine, phenol, phenylephrine, phenylpropanolamine, piperonyl butoxide, podophyllin, podofilox, povidone iodine, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, and zinc pyrithione.

12. The composition as claimed in claim 1, wherein the composition further comprises one or more additional ingredients selected from the group consisting of hydroxycarboxylic acids, O-acetyl-hydroxycarboxylic acids, oligosaccharide aldonic acids, N-acylamino sugars, N-acylamino acids, and mixtures and combinations thereof.

13. The composition as claimed in claim 1, wherein the phenyl-glycine compound is selected from the group consisting of phenyl-glycine, phenyl-glycinamide, phenyl-glycine methyl ester, phenyl-glycine ethyl ester, phenyl-glycine propyl ester, and mixtures thereof.

14. The composition as claimed in claim 1, wherein the phenyl-glycine compound is selected from the group consisting of N-acetyl-phenyl-glycine, N-acetyl-phenyl-glycinamide, N-acetyl-phenyl-glycine methyl ester, N-acetyl-phenyl-glycine ethyl ester, and mixtures thereof.

15. The composition as claimed in claim 1, wherein the phenyl-glycine compound is selected from the group consisting of N-formyl-phenyl-glycine, N-formyl-phenyl-glycinamide, N-formyl-phenyl-glycine methyl ester, N-formyl-phenyl-glycine ethyl ester, and mixtures thereof.

16. The composition as claimed in claim 1, wherein the phenyl-glycine compound is selected from the group consisting of N-propanoyl-phenyl-glycine, N-propanoyl-phenyl-glycinamide, N-propanoyl-phenyl-glycine methyl ester, N-propanoyl-phenyl-glycine ethyl ester, and mixtures thereof.

17. The composition as claimed in claim 1, wherein the phenyl-glycine compound is selected from the group consisting of 4-hydroxyphenyl-glycine, 4-hydroxyphenyl-glycinamide, 4-hydroxyphenyl-glycine methyl ester, 4-hydroxyphenyl-glycine ethyl ester, and mixtures thereof.

18. The composition as claimed in claim 1, wherein the phenyl-glycine compound is selected from the group consisting of N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, and mixtures thereof.

19. The composition as claimed in claim 1, wherein the phenyl-glycine compound is selected from the group consisting of N-formyl-4-hydroxyphenyl-glycine, N-formyl-4-hydroxyphenyl-glycinamide, N-formyl-4-hydroxyphenyl-glycine methyl ester, N-formyl-4-hydroxyphenyl-glycine ethyl ester, and mixtures thereof.

20. The composition as claimed in claim 1, wherein the phenyl-glycine compound is selected from the group consisting of N-propanoyl-4-hydroxyphenyl-glycine, N-propanoyl-4-hydroxyphenyl-glycinamide, N-propanoyl-4-hydroxyphenyl-glycine methyl ester, N-propanoyl-4-hydroxyphenyl-glycine ethyl ester, and mixtures thereof.

21. The composition as claimed in claim 1, wherein the phenyl-glycine compound is selected from the group consisting of 4-acetoxyphenyl-glycine, 4-acetoxyphenyl-glycinamide, 4-acetoxyphenyl-glycine methyl ester, 4-acetoxyphenyl-glycine ethyl ester, and mixtures thereof.

22. The composition as claimed in claim 1, wherein the phenyl-glycine compound is selected from the group consisting of N-acetyl-4-acetoxyphenyl-glycine, N-acetyl-4-acetoxyphenyl-glycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, and mixtures thereof.

23. The composition as claimed in claim 1, wherein the phenyl-glycine compound is selected from the group consisting of N-formyl-4-acetoxyphenyl-glycine, N-formyl-4-acetoxyphenyl-glycinamide, N-formyl-4-acetoxyphenyl-glycine methyl ester, N-formyl-4-acetoxyphenyl-glycine ethyl ester, N-formyl-4-acetoxyphenyl-glycine propyl ester, and mixtures thereof.

24. The composition as claimed in claim 1, wherein the phenyl-glycine compound is selected from the group consisting of N-propanoyl-4-acetoxyphenyl-glycine, N-propanoyl-4-acetoxyphenyl-glycinamide, N-propanoyl-4-acetoxyphenyl-glycine methyl ester, N-propanoyl-4-acetoxyphenyl-glycine ethyl ester, N-propanoyl-4-acetoxyphenyl-glycine propyl ester, and mixtures thereof.

25. The composition as claimed in claim 1, wherein the phenyl-glycine compound is selected from the group consisting of 2-hydroxyphenyl-glycine, 2-hydroxyphenyl-glycinamide, 2-hydroxyphenyl-glycine methyl ester, 2-hydroxyphenyl-glycine ethyl ester, and mixtures thereof.

26. The composition as claimed in claim 1, wherein the phenyl-glycine compound is selected from the group consisting of N-acetyl-2-hydroxyphenyl-glycine, N-acetyl-2-hydroxyphenyl-glycinamide, N-acetyl-2-hydroxyphenyl-glycine methyl ester, N-acetyl-2-hydroxyphenyl-glycine ethyl ester, and mixtures thereof.

27. The composition as claimed in claim 1, wherein the phenyl-glycine compound is selected from the group consisting of N-formyl-2-hydroxyphenyl-glycine, N-formyl-2-hydroxyphenyl-glycinamide, N-formyl-2-hydroxyphenyl-glycine methyl ester, N-formyl-2-hydroxyphenyl-glycine ethyl ester, and mixtures thereof.

28. The composition as claimed in claim 1, wherein the phenyl-glycine compound is selected from the group consisting of N-propanoyl-2-hydroxyphenyl-glycine, N-propanoyl-2-hydroxyphenyl-glycinamide, N-propanoyl-2-hydroxyphenyl-glycine methyl ester, N-propanoyl-2-hydroxyphenyl-glycine ethyl ester, and mixtures thereof.

29. The composition as claimed in claim 1, wherein the phenyl-glycine compound is selected from the group consisting of N-acetyl-2-acetoxyphenyl-glycine, N-acetyl-2-acetoxyphenyl-glycinamide, N-acetyl-2-acetoxyphenyl-glycine methyl ester, N-acetyl-2-acetoxyphenyl-glycine ethyl ester, N-acetyl-2-acetoxyphenyl-glycine propyl ester, and mixtures thereof.

30. The composition as claimed in claim 1, wherein the phenyl-glycine compound is selected from the group consisting of N-formyl-2-acetoxyphenyl-glycine, N-formyl-2-acetoxyphenyl-glycinamide, N-formyl-2-acetoxyphenyl-glycine methyl ester, N-formyl-2-acetoxyphenyl-glycine ethyl ester; N-formyl-2-acetoxyphenyl-glycine propyl ester, and mixtures thereof.

31. The composition as claimed in claim 1, wherein the phenyl-glycine compound is selected from the group consisting of N-propanoyl-2-acetoxyphenyl-glycine, N-propanoyl-2-acetoxyphenyl-glycinamide, N-propanoyl-2-acetoxyphenyl-glycine methyl ester, N-propanoyl-2-acetoxyphenyl-glycine ethyl ester, N-propanoyl-2-acetoxyphenyl-glycine propyl ester, and mixtures thereof.

32. The composition as claimed in claim 1, wherein the phenyl-glycine compound is selected from the group consisting of 3-hydroxyphenyl-glycine, 3-hydroxyphenyl-glycinamide, 3-hydroxyphenyl-glycine methyl ester, 3-hydroxyphenyl-glycine ethyl ester, and mixtures thereof.

33. The composition as claimed in claim 1, wherein the phenyl-glycine compound is selected from the group consisting of N-acetyl-3-hydroxyphenyl-glycine, N-acetyl-3-hydroxyphenyl-glycinamide, N-acetyl-3-hydroxyphenyl-glycine methyl ester, N-acetyl-3-hydroxyphenyl-glycine ethyl ester, and mixtures thereof.

34. The composition as claimed in claim 1, wherein the phenyl-glycine compound is selected from the group consisting of N-formyl-3-hydroxyphenyl-glycine, N-formyl-3-hydroxyphenyl-glycinamide, N-formyl-3-hydroxyphenyl-glycine methyl ester, N-formyl-3-hydroxyphenyl-glycine ethyl ester, and mixtures thereof.

35. The composition as claimed in claim 1, wherein the phenyl-glycine compound is selected from the group consisting of N-propanoyl-3-hydroxyphenyl-glycine, N-propanoyl-3-hydroxyphenyl-glycinamide, N-propanoyl-3-hydroxyphenyl-glycine methyl ester, N-propanoyl-3-hydroxyphenyl-glycine ethyl ester, and mixtures thereof.

36. The composition as claimed in claim 1, wherein the phenyl-glycine compound is selected from the group consisting of N-acetyl-3-acetoxyphenyl-glycine, N-acetyl-3-acetoxyphenyl-glycinamide, N-acetyl-3-acetoxyphenyl-glycine methyl ester, N-acetyl-3-acetoxyphenyl-glycine ethyl ester, N-acetyl-3-acetoxyphenyl-glycine propyl ester, and mixtures thereof.

37. The composition as claimed in claim 1, wherein the phenyl-glycine compound is selected from the group consisting of N-formyl-3-acetoxyphenyl-glycine, N-formyl-3-acetoxyphenyl-glycinamide, N-formyl-3-acetoxyphenyl-glycine methyl ester, N-formyl-3-acetoxyphenyl-glycine ethyl ester, N-formyl-3-acetoxyphenyl-glycine propyl ester, and mixtures thereof.

38. The composition as claimed in claim 1, wherein the phenyl-glycine compound is selected from the group consisting of N-propanoyl-3-acetoxyphenyl-glycine, N-propanoyl-3-acetoxyphenyl-glycinamide, N-propanoyl-3-acetoxyphenyl-glycine methyl ester, N-propanoyl-3-acetoxyphenyl-glycine ethyl ester, N-propanoyl-3-acetoxyphenyl-glycine propyl ester, and mixtures thereof.

39. The composition as claimed in claim 1, wherein the phenyl-glycine compound is selected from the group consisting of 3,4-dihydroxyphenyl-glycine, 3,4-dihydroxyphenyl-glycinamide, 3,4-dihydroxyphenyl-glycine methyl ester, 3,4-dihydroxyphenyl-glycine ethyl ester, and mixtures thereof.

40. The composition as claimed in claim 1, wherein the phenyl-glycine compound is selected from the group consisting of N-acetyl-3,4-dihydroxyphenyl-glycine, N-acetyl-3,4-dihydroxyphenyl-glycinamide, N-acetyl-3,4-dihydroxyphenyl-glycine methyl ester, N-acetyl-3,4-dihydroxyphenyl-glycine ethyl ester, and mixtures thereof.

41. The composition as claimed in claim 1, wherein the phenyl-glycine compound is selected from the group consisting of N-acetyl-3,4-diacetoxyphenyl-glycine, N-acetyl-3,4-diacetoxyphenyl-glycinamide, N-acetyl-3,4-diacetoxyphenyl-glycine methyl ester, N-acetyl-3,4-diacetoxyphenyl-glycine ethyl ester, and mixtures thereof.

42. A method of improving, treating, ameliorating, alleviating, or reducing cosmetic conditions and dermatological disorders comprising topically applying an effective amount of a composition comprising a phenyl glycine derivative represented by the following general formula:

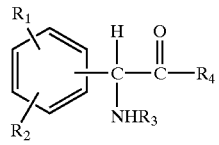

wherein, $R_1$ and $R_2$ are independently H, I, F, Cl, Br, OH, SH, $NH_2$, $NHNH_2$, alkyl, aralkyl, alkoxy, acetoxy, acyloxy group having 1 to 9 carbon atoms, and being attached at the 2, 3 or 4 position of the phenyl group, whereby when $R_1$ and/or $R_2$ are OH, SH, $NH_2$, they may be acetylated or acylated with 1 to 9 carbon atoms; $R_3$ is H, formyl, acetyl, propanoyl, acyl, alkyl, aralkyl or an aryl group having 1 to 9 carbon atoms; $R_4$ is OH, $NH_2$, NHOH, $NHNH_2$, or OR; where R is an alkyl, aralkyl or aryl group having 1 to 9 carbon atoms; the H attached to any carbon or nitrogen atom may be substituted by I, F, Cl, Br, OH, SH, $NH_2$, $NHNH_2$, an alkyl, aralkyl, alkoxy or acyl group having 1 to 9 carbon atoms. Phenyl-glycine and its derivatives may be present as isomeric D or L, non-isomeric or racemic DL, as a free acid, salt, lactone, amide or ester form.

43. The method as claimed in claim 42, wherein the phenyl-glycine derivative is selected from the group consisting of 4-hydroxyphenyl-glycine, 4-hydroxyphenyl-glycinamide, 4-hydroxyphenyl-glycine methyl ester, 4-hydroxyphenyl-glycine ethyl ester, 4-hydroxyphenyl-glycine propyl ester, 4-hydroxyphenyl-glycine isopropyl ester, N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, N-acetyl-4-hydroxyphenyl-glycine propyl ester, N-acetyl-4-hydroxyphenyl-glycine isopropyl ester; N-acetyl-4-acetoxyphenyl-glycine, N-acetyl-4-acetoxyphenyl-glycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, N-acetyl-4-acetoxyphenyl-glycine isopropyl ester, 4-acetoxyphenyl-glycinamide, and mixtures thereof.

44. The method as claimed in claim 42, wherein the phenyl-glycine derivative is N-Acetyl-4-hydroxyphenyl-glycinamide.

45. The method as claimed in claim 42, wherein the phenyl-glycine derivative is N-acetyl-4-acetoxyphenyl-glycinamide.

46. The method as claimed in claim 42, wherein the phenyl-glycine derivative is 4-hydroxyphenyl-glycine methyl ester.

47. The method as claimed in claim 42, wherein the phenyl-glycine derivative is 4-hydroxyphenyl-glycine ethyl ester.

48. The method as claimed in claim 42, wherein the phenyl-glycine derivative is N-acetyl-4-hydroxyphenyl-glycine ethyl ester.

49. The method as claimed in claim 42, wherein the composition is selected from the group consisting of a solution, a gel, a lotion, a cream, an ointment, a shampoo, a spray, a stick, a powder, a masque, a mouth rinse or wash, a vaginal gel or preparation, and mixtures and combinations thereof.

50. The method as claimed in claim 42, wherein the composition further comprises one or more additional ingredients selected from the group consisting of cosmetic agents, pharmaceutical agents, topical agents, and mixtures and combinations thereof.

51. The method as claimed in claim 50, wherein the one or more additional ingredients is selected from the group consisting of agents that improve or eradicate age spots, keratoses, and/or wrinkles; hydroxyacids, ketoacids and related compounds; phenyl alpha acyloxyalkanoic acids and derivatives; N-acetyl-aldosamines, N-acetylamino acids and related N-acetyl compounds; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratotic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; astringents; cleansing agents; corn, callus and wart removing agents; topical cardiovascular agents; vitamins; corticosteroids; tanning agents; humectants, hormones; retinoids; gum disease or oral care agents; dipilating agents; and other dermatologicals.

52. The method as claimed in claim 50, wherein the one or more additional ingredients is selected from the group consisting of aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), aminocaproic acid, aminosalicylic acid, amitriptyline, anthralin, ascorbic acid, ascorbyl palmitate, atropine, azelaic acid, bacitracin, bemegride, beclomethasone dipropionate, benzophenone, benzoyl peroxide, betamethasone dipropionate, betamethasone valerate, brompheniramine, bupivacaine, butoconazole, calcipotriene, camphor, capsaicin, carbamide peroxide, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxycycline, doxepin, doxylamine, dyclonine, econazole, erythromycin, estradiol, ethinyl estradiol, fluocinonide, fluocinolone acetonide, 5-fluorouracil, griseofulvin, guaifenesin, haloprogin, hexylresorcinol, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichthammol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, oxybenzone, oxiconazole, oxymetazoline, padimate O, permethrin, pheniramine, phenol, phenylephrine, phenylpropanolamine, piperonyl butoxide, podophyllin, podofilox, povidone iodine, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, and zinc pyrithione.

53. The method as claimed in claim 42, wherein the composition further comprises one or more additional ingredients selected from the group consisting of hydroxycarboxylic acids, O-acetyl-hydroxycarboxylic acids, oligosaccharide aldonic acids, N-acylamino sugars, N-acylamino acids, and mixtures and combinations thereof.

54. The method as claimed in claim 42, wherein the method is useful for general care of the skin, reducing and soothing mucosa and skin erythema, inflammation or reaction caused by internal or external factors, treatment and healing of skin, hair, nail; nasal, oral and vaginal mucosa including treatment, healing and prevention of cosmetic conditions and dermatological indications as well as cosmetic and clinical signs of changes associated with intrinsic aging, or the damages caused by extrinsic factors as sunlight, radiations, air pollution, wind, cold, dampness, heat, chemicals, smoke, and cigarette smoking.

55. The method as claimed in claim 54, wherein the method is useful for treating blemished, irritated, inflamed, unhealthy, damaged or abnormal mucosa, skin, hair, nail, nostril, ear canal or vaginal conditions; oral or gum disease; disturbed keratinization; defective syntheses or repair of dermal components, and changes associated with intrinsic and extrinsic aging of skin, nail and hair, dryness of the skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans and elastin as well as diminished levels of such components in the dermis; cellulite; stretch marks; skin lines; fine lines; wrinkles; thinning of skin, nail plate and hair; skin thickening due to elastosis of photoaging, loss or reduction of skin, nail and hair resiliency, elasticity and recoilability; lack of skin, nail and hair lubricants and luster; dull and older-looking skin, nail and hair; fragility and splitting of nail and hair.

56. The method as claimed in claim 42, wherein the cosmetic conditions and dermatological disorders are selected from the group consisting of wound healing, general and specific conditions and indications involving skin, hair, nail, gum, oral, vaginal and anal mucosa, disturbed keratinization, inflammation, defective syntheses of dermal components, changes associated with intrinsic and extrinsic aging of skin, nail and hair, and those indications that include: dryness or looseness of skin, nail, and hair; xerosis; ichthyosis; palmar and plantar hyperkeratoses; uneven and rough surface of skin, nail, and hair; dandruff; Darier's disease; lichen simplex chronicus; keratoses; acne; pseudofolliculitis barbae; dermatoses; eczema; psoriasis; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans, and elastin, diminished levels of these components in the dermis; stretch marks; skin lines; fine lines; wrinkles; thinning of skin, nail plate, and hair; skin thickening due to elastosis of photoaging; loss or reduction of skin, nail, and hair resiliency, elasticity and recoilability; lack of skin, nail, and hair lubricants and luster; dull and older-looking skin, nail, and hair; fragility and splitting of nail and hair, and skin lightening.

57. The method as claimed in claim 42, wherein the cosmetic condition or dermatological disorder is skin changes associated with aging.

58. The method as claimed in claim 57, wherein the skin changes associated with aging are selected from the group consisting of progressive thinning of skin, fragile skin, deepening of skin lines and fine lines, wrinkles including fine and coarse wrinkles, lusterless skin surface, coarse and uneven skin, loss of skin elasticity and recoilability, blemished and leathery skin, loss of skin lubricating substances, increased numbers of blotches and mottles, nodules, precancerous lesions, pigmented spots and mottled skin, changes in qualities and quantities of collagen and elastic fibers, solar elastosis, decrease in collagen fibers, diminution in the number and diameter of elastic fibers in the papillary dermis, atrophy of the dermis, stretch marks, reduction in subcutaneous adipose tissue and deposition of abnormal elastic materials in the upper dermis, yellowing skin, telangiectatic skin and older-looking skin.

59. The method as claimed in claim 42, wherein the phenyl-glycine compound is selected from the group consisting of phenyl-glycine, phenyl-glycinamide, phenyl-glycine methyl ester, phenyl-glycine ethyl ester, phenyl-glycine propyl ester, and mixtures thereof.

60. The method as claimed in claim 42, wherein the phenyl-glycine compound is selected from the group consisting of N-acetyl-phenyl-glycine, N-acetyl-phenyl-glycinamide, N-acetyl-phenyl-glycine methyl ester, N-acetyl-phenyl-glycine ethyl ester, and mixtures thereof.

61. The method as claimed in claim 42, wherein the phenyl-glycine compound is selected from the group consisting of N-formyl-phenyl-glycine, N-formyl-phenyl-glycinamide, N-formyl-phenyl-glycine methyl ester, N-formyl-phenyl-glycine ethyl ester, and mixtures thereof.

62. The method as claimed in claim 42, wherein the phenyl-glycine compound is selected from the group consisting of N-propanoyl-phenyl-glycine, N-propanoyl-phenyl-glycinamide, N-propanoyl-phenyl-glycine methyl ester, N-propanoyl-phenyl-glycine ethyl ester, and mixtures thereof.

63. The method as claimed in claim 42, wherein the phenyl-glycine compound is selected from the group consisting of 4-hydroxyphenyl-glycine, 4-hydroxyphenyl-glycinamide, 4-hydroxyphenyl-glycine methyl ester, 4-hydroxyphenyl-glycine ethyl ester, and mixtures thereof.

64. The method as claimed in claim 42, wherein the phenyl-glycine compound is selected from the group consisting of N-acetyl-4-hydroxyphenyl-glycine, N-acetyl-4-hydroxyphenyl-glycinamide, N-acetyl-4-hydroxyphenyl-glycine methyl ester, N-acetyl-4-hydroxyphenyl-glycine ethyl ester, and mixtures thereof.

65. The method as claimed in claim 42, wherein the phenyl-glycine compound is selected from the group consisting of N-formyl-4-hydroxyphenyl-glycine, N-formyl-4-hydroxyphenyl-glycinamide, N-formyl-4-hydroxyphenyl-glycine methyl ester, N-formyl-4-hydroxyphenyl-glycine ethyl ester, and mixtures thereof.

66. The method as claimed in claim 42, wherein the phenyl-glycine compound is selected from the group consisting of N-propanoyl-4-hydroxyphenyl-glycine, N-propanoyl-4-hydroxyphenyl-glycinamide, N-propanoyl-4-hydroxyphenyl-glycine methyl ester, N-propanoyl-4-hydroxyphenyl-glycine ethyl ester, and mixtures thereof.

67. The method as claimed in claim 42, wherein the phenyl-glycine compound is selected from the group consisting of 4-acetoxyphenyl-glycine, 4-acetoxyphenyl-glycinamide, 4-acetoxyphenyl-glycine methyl ester, 4-acetoxyphenyl-glycine ethyl ester, and mixtures thereof.

68. The method as claimed in claim 42, wherein the phenyl-glycine compound is selected from the group consisting of N-acetyl-4-acetoxyphenyl-glycine, N-acetyl-4-acetoxyphenyl-glycinamide, N-acetyl-4-acetoxyphenyl-glycine methyl ester, N-acetyl-4-acetoxyphenyl-glycine ethyl ester, N-acetyl-4-acetoxyphenyl-glycine propyl ester, and mixtures thereof.

69. The method as claimed in claim 42, wherein the phenyl-glycine compound is selected from the group consisting of N-formyl-4-acetoxyphenyl-glycine, N-formyl-4-acetoxyphenyl-glycinamide, N-formyl-4-acetoxyphenyl-glycine methyl ester, N-formyl-4-acetoxyphenyl-glycine ethyl ester, N-formyl-4-acetoxyphenyl-glycine propyl ester, and mixtures thereof.

70. The method as claimed in claim 42, wherein the phenyl-glycine compound is selected from the group consisting of N-propanoyl-4-acetoxyphenyl-glycine, N-propanoyl-4-acetoxyphenyl-glycinamide, N-propanoyl-4-acetoxyphenyl-glycine methyl ester, N-propanoyl-4-acetoxyphenyl-glycine ethyl ester, N-propanoyl-4-acetoxyphenyl-glycine propyl ester, and mixtures thereof.

71. The method as claimed in claim 42, wherein the phenyl-glycine compound is selected from the group consisting of 2-hydroxyphenyl-glycine, 2-hydroxyphenyl-glycinamide, 2-hydroxyphenyl-glycine methyl ester, 2-hydroxyphenyl-glycine ethyl ester, and mixtures thereof.

72. The method as claimed in claim 42, wherein the phenyl-glycine compound is selected from the group consisting of N-acetyl-2-hydroxyphenyl-glycine, N-acetyl-2-hydroxyphenyl-glycinamide, N-acetyl-2-hydroxyphenyl-glycine methyl ester, N-acetyl-2-hydroxyphenyl-glycine ethyl ester, and mixtures thereof.

73. The method as claimed in claim 42, wherein the phenyl-glycine compound is selected from the group consisting of N-formyl-2-hydroxyphenyl-glycine, N-formyl-2-hydroxyphenyl-glycinamide, N-formyl-2-hydroxyphenyl-glycine methyl ester, N-formyl-2-hydroxyphenyl-glycine ethyl ester, and mixtures thereof.

74. The method as claimed in claim 42, wherein the phenyl-glycine compound is selected from the group consisting of N-propanoyl-2-hydroxyphenyl-glycine, N-propanoyl-2-hydroxyphenyl-glycinamide, N-propanoyl-2-hydroxyphenyl-glycine methyl ester, N-propanoyl-2-hydroxyphenyl-glycine ethyl ester, and mixtures thereof.

75. The method as claimed in claim 42, wherein the phenyl-glycine compound is selected from the group consisting of N-acetyl-2-acetoxyphenyl-glycine, N-acetyl-2-acetoxyphenyl-glycinamide, N-acetyl-2-acetoxyphenyl-glycine methyl ester, N-acetyl-2-acetoxyphenyl-glycine ethyl ester, N-acetyl-2-acetoxyphenyl-glycine propyl ester, and mixtures thereof.

76. The method as claimed in claim 42, wherein the phenyl-glycine compound is selected from the group consisting of N-formyl-2-acetoxyphenyl-glycine, N-formyl-2-acetoxyphenyl-glycinamide, N-formyl-2-acetoxyphenyl-glycine methyl ester, N-formyl-2-acetoxyphenyl-glycine ethyl ester; N-formyl-2-acetoxyphenyl-glycine propyl ester, and mixtures thereof.

77. The method as claimed in claim 42, wherein the phenyl-glycine compound is selected from the group consisting of N-propanoyl-2-acetoxyphenyl-glycine, N-propanoyl-2-acetoxyphenyl-glycinamide, N-propanoyl-2-acetoxyphenyl-glycine methyl ester, N-propanoyl-2-acetoxyphenyl-glycine ethyl ester, N-propanoyl-2-acetoxyphenyl-glycine propyl ester, and mixtures thereof.

78. The method as claimed in claim 42, wherein the phenyl-glycine compound is selected from the group consisting of 3-hydroxyphenyl-glycine, 3-hydroxyphenyl-glycinamide, 3-hydroxyphenyl-glycine methyl ester, 3-hydroxyphenyl-glycine ethyl ester, and mixtures thereof.

79. The method as claimed in claim 42, wherein the phenyl-glycine compound is selected from the group consisting of N-acetyl-3-hydroxyphenyl-glycine, N-acetyl-3-hydroxyphenyl-glycinamide, N-acetyl-3-hydroxyphenyl-glycine methyl ester, N-acetyl-3-hydroxyphenyl-glycine ethyl ester, and mixtures thereof.

80. The method as claimed in claim 42, wherein the phenyl-glycine compound is selected from the group consisting of N-formyl-3-hydroxyphenyl-glycine, N-formyl-3-hydroxyphenyl-glycinamide, N-formyl-3-hydroxyphenyl-glycine methyl ester, N-formyl-3-hydroxyphenyl-glycine ethyl ester, and mixtures thereof.

81. The method as claimed in claim 42, wherein the phenyl-glycine compound is selected from the group consisting of N-propanoyl-3-hydroxyphenyl-glycine, N-propanoyl-3-hydroxyphenyl-glycinamide, N-propanoyl-3-hydroxyphenyl-glycine methyl ester, N-propanoyl-3-hydroxyphenyl-glycine ethyl ester, and mixtures thereof.

82. The method as claimed in claim 42, wherein the phenyl-glycine compound is selected from the group consisting of N-acetyl-3-acetoxyphenyl-glycine, N-acetyl-3-acetoxyphenyl-glycinamide, N-acetyl-3-acetoxyphenyl-glycine methyl ester, N-acetyl-3-acetoxyphenyl-glycine ethyl ester, N-acetyl-3-acetoxyphenyl-glycine propyl ester, and mixtures thereof.

83. The method as claimed in claim 42, wherein the phenyl-glycine compound is selected from the group consisting of N-formyl-3-acetoxyphenyl-glycine, N-formyl-3-acetoxyphenyl-glycinamide, N-formyl-3-acetoxyphenyl-glycine methyl ester, N-formyl-3-acetoxyphenyl-glycine ethyl ester, N-formyl-3-acetoxyphenyl-glycine propyl ester, and mixtures thereof.

84. The method as claimed in claim 42, wherein the phenyl-glycine compound is selected from the group consisting of N-propanoyl-3-acetoxyphenyl-glycine, N-propanoyl-3-acetoxyphenyl-glycinamide, N-propanoyl-3-acetoxyphenyl-glycine methyl ester, N-propanoyl-3- acetoxyphenyl-glycine ethyl ester, N-propanoyl-3-acetoxyphenyl-glycine propyl ester, and mixtures thereof.

85. The method as claimed in claim 42, wherein the phenyl-glycine compound is selected from the group consisting of 3,4-dihydroxyphenyl-glycine, 3,4-dihydroxyphenyl-glycinamide, 3,4-dihydroxyphenyl-glycine methyl ester, 3,4-dihydroxyphenyl-glycine ethyl ester, and mixtures thereof.

86. The method as claimed in claim 42, wherein the phenyl-glycine compound is selected from the group consisting of N-acetyl-3,4-dihydroxyphenyl-glycine, N-acetyl-3,4-dihydroxyphenyl-glycinamide, N-acetyl-3,4-dihydroxyphenyl-glycine methyl ester, N-acetyl-3,4-dihydroxyphenyl-glycine ethyl ester, and mixtures thereof.

87. The method as claimed in claim 42, wherein the phenyl-glycine compound is selected from the group consisting of N-acetyl-3,4-diacetoxyphenyl-glycine, N-acetyl-3,4-diacetoxyphenyl-glycinamide, N-acetyl-3,4-diacetoxyphenyl-glycine methyl ester, N-acetyl-3,4-diacetoxyphenyl-glycine ethyl ester, and mixtures thereof.

* * * * *